United States Patent
Gerson et al.

(10) Patent No.: US 7,048,952 B2
(45) Date of Patent: May 23, 2006

(54) FORMULATION FOR INHIBITING FUNGAL AND MICROBIAL GROWTH COMPRISING MORINDA CITRIFOLIA PUREE JUICE

(75) Inventors: Scott Gerson, Brewster, NY (US); Afa Kehaati Palu, Orem, UT (US); Bing-Nan Zhou, Sandy, UT (US); Chen Su, West Jordan, UT (US); Claude Jarakae Jensen, Cedar Hills, UT (US); Stephen P. Story, Alpine, UT (US); Robert V. Ogden, Cedar Hills, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 10/439,596

(22) Filed: May 16, 2003

(65) Prior Publication Data

US 2003/0225005 A1 Dec. 4, 2003

Related U.S. Application Data

(60) Provisional application No. 60/382,246, filed on May 21, 2002.

(51) Int. Cl.
*A61K 35/78* (2006.01)
(52) U.S. Cl. ...................................... 424/725
(58) Field of Classification Search ................ 424/725, 424/195.1
See application file for complete search history.

(56) References Cited

OTHER PUBLICATIONS

Conquer et al. Supplementation with Quercetin Markedly Increases Plasma Quercetin Concentration Without Effect on Selected Risk Factors for Heart Disease in Healthy Subjects: The Journal of Nutrition; Bethesda (1998) Issue 3, p. 593, 5 pages, pp. 1-7 of proquest direct printout.*
El-Gammal Antimicrobial Activities of Some Flavonoid Compounds; Zentralbl. Mikrobiol. 141 (1986) pp. 561-565.*
Tipofallsorts.com Noni Juice; URL <www.tipsofallsorts.com/noni.html>, 1999 pates 1-11.*

* cited by examiner

*Primary Examiner*—Patricia Leith
(74) *Attorney, Agent, or Firm*—Kirton & McConkie; Michael F. Krieger

(57) ABSTRACT

The present invention relates to antifungal and antibacterial activity of processed *Morinda citrifolia* products, as well as from various fractions of extracts from these processed products and the *Morinda citrifolia L.* plant, and related methods to determine mean inhibitory concentrations. In particular, the present invention relates to ethanol, methanol and ethyl acetate extracts from *Morinda citrifolia L.* and their inhibitory activities on common fungi and bacteria and the identification of mean inhibitory concentrations.

4 Claims, No Drawings

FORMULATION FOR INHIBITING FUNGAL AND MICROBIAL GROWTH COMPRISING MORINDA CITRIFOLIA PUREE JUICE

RELATED APPLICATIONS

This application claims priority to U.S. Provisional Application Ser. No. 60/382,246, filed May 21, 2002, and entitled, "Antifungal Activity and Mean Inhibitory Concentration of Selected Extracts from *Morinda citrifolia L.* and related methods."

BACKGROUND

1. Field of the Invention

The present invention relates to antifungal activity of extracts from *Morinda citrifolia L.* and formulated in a naturaceutical composition. In particular, the present invention relates to mean inhibitory concentrations (MIC) of selected *Morinda citrifolia* puree and juice and various compositions or formulations comprising one or more *Morinda citrifolia* products for treatment of fungal activity in mammals.

2. Background of the Invention and Related Art

Despite the existence of tens of thousands of antimicrobial compounds, the ability of microorganisms to develop resistance to even the most recent and powerful antimicrobial compounds or treatments is amazingly rapid. In order to keep pace with this ever increasing need for new antimicrobials, it is imperative that new compounds be discovered. Some of these may even come from unusual sources. A review of the history of the development of antimicrobials indicates that there are actually very few instances of new classes of compounds being isolated using a "top down" approach involving massive screening. Most of the antibiotics available today have actually been created using a "bottom up" approach, meaning in short that they have been synthesized from component parts upon identification and isolation of a single structure.

Perhaps the most famous example of this is Penicillin. Contrary to popular belief, the antimicrobial properties of *Penicillium* molds had been known since the 1850's. In 1928 Alexander Fleming made the observation that the mold was producing a chemical substance that inhibited staphylococcal growth. Despite the fact that penicillin represented a measurable portion of the products produced during *Penicillium* fermentation, it took until 1945 before the structure was actually identified. It took approximately ten more years, before penicillin could be obtained in a form that could allow its chemical modification. Once this step had been accomplished however, it paved the way for hundreds of useful penicillin class antibiotics. These included methicillin, oxacillin, ampiciflin, piperacillin, and many others.

Still today, there are other types or strains of bacteria and fungus that are harmful to the health of the individuals they infect. As such, there remains a need for new discoveries and treatment solutions and methods for combating these bodily invaders.

SUMMARY AND OBJECTS OF THE INVENTION

The present invention relates to antifungal and antibacterial activity of extracts from *Morinda citrifolia L.* and related methods to determine mean inhibitory concentrations. In particular, the present invention relates to ethanol, methanol and ethyl acetate extracts from *Morinda citrifolia L.* and their inhibitory activities on common fungi and bacteria and the identification of mean inhibitory concentrations.

Implementation of the present invention takes place in association with the utilization of juice, puree, and other extracts or parts from the plant known as *Morinda citrifolia L.*

In accordance with the invention as embodied and broadly described herein, the present invention features various methods for inhibiting, preventing, and destroying existing harmful fungi and microbial activity and growth using active compounds and/or ingredients extracted from and existing within one or more processed *Morinda citrifolia* products. The *Morinda citrifolia* products are preferably contained within a naturaceutical formulation designed for internalization within the body of a mammal.

In one exemplary embodiment, the method comprises the step of introducing into a mammal a composition comprising a processed *Morinda citrifolia* product present in an amount between about 0.01 and 100 percent by weight, wherein the *Morinda citrifolia* product comprises various components that effectuate antifungal and antibacterial or antimicrobial activity. These components may be fractioned out of the several Morinda citrifolia products and concentrated into a naturaceutical or other formulation for treatment of fungal or bacterial infections.

The step of introducing the naturaceutical composition may be achieved using a variety of methods including, but not limited to, orally administering (e.g. drinking) the naturaceutical, transdermally introducing the naturaceutical (e.g. a skin patch), systemically introducing the naturaceutical (e.g. via an intravenous pump), or injecting the naturaceutical into a designated and specific area.

The processed *Morinda citrifolia* product may comprise a variety of types, including, but not limited to, processed *Morinda citrifolia* fruit juice, processed *Morinda citrifolia* puree juice, processed *Morinda citrifolia* dietary fiber, processed *Morinda citrifolia* oil, processed *Morinda citrifolia* fruit juice concentrate, processed *Morinda citrifolia* puree juice concentrate, and processed *Morinda citrifolia* oil extract.

The present invention also features a naturaceutical formulation for inhibiting and treating fungi and microbial activity and growth, wherein the naturaceutical formulation comprises at least one or more processed *Morinda citrifolia* products. Within the processed *Morinda citrifolia* products are *Morinda citrifolia* fractions or extracts that specifically exhibit antifungal and antimicrobial activities. The naturaceutical formulation also may comprise other natural ingredients, such as other fruit juices, water, etc.

DETAILED DESCRIPTION OF THE PREFERRED EMBODIMENTS

It will be readily understood that the compositions and formulations of the present invention, as generally described herein, could be designed in and could comprise a wide variety of different variations. Thus, the following more detailed description of the embodiments of the formulations and methods of the present invention is not intended to limit the scope of the invention, as claimed, but is merely representative of the presently preferred embodiments of the invention.

The present invention relates to methods for determining the activity and mean inhibitory concentration of extracts of *Morinda citrifolia L.* against common fungi and bacteria. In particular, the present invention relates to ethanol, methanol and ethyl acetate extracts and various fractions from *Morinda citrifolia L.* and the antifungal and antibacterial effect of these in regards to their determined mean inhibitory concentrations and mean lethal concentrations as existing within a naturaceutical formulation, which concentrations are based upon various experimental studies.

General Discussion of *Morinda citrifolia* and the Methods Used to Produce Processed *Morinda citrifolia* Products The Indian Mulberry or Noni plant, known scientifically as *Morinda citrifolia L.* (*Morinda citrifolia*), is a shrub, or small or medium-sized tree 3 to 10 meters high that grows in tropical coastal regions around the world. The plant is native to Southeast Asia and has spread in early times to a vast area from India to eastern Polynesia. It grows randomly in the wild, and it has been cultivated in plantations and small individual growing plots. *Morinda citrifolia* has somewhat rounded branches and evergreen, opposite (or spuriously alternate), dark, glossy, wavy, prominently-veined leaves. The leaves are broadly elliptic to oblong, pointed at both ends, 10–30 cm in length and 5–15 cm wide.

*Morinda citrifolia* flowers are contained in a fleshy, globose, head-like cluster and are small, white, 3 to 5 lobed, tubular, fragrant, and about 1.25 cm long. The flowers develop into compound fruits composed of many small drupes fused into an ovoid, ellipsoid or roundish, lumpy body, 5–10 cm long, 5–7 cm thick, with waxy, white or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged, 2-celled stones, each containing about 4 seeds. At maturity, they are creamy-white and edible, but have an unpleasant taste and odor. When fully ripe, the fruit has a pronounced odor like rancid cheese.

Although the fruit has been eaten by several nationalities as food, one common use of the Indian mulberry plant was as a red and yellow dye source. However, *Morinda citrifolia* has also been discovered to contain health enhancing compounds and/or enzymes that, among other things, aids in easing inflammation, calming feelings of anxiety, supporting weight management, and promoting circulatory health in humans. Moreover, *Morinda citrifolia* is considered to be an adaptogenic herb, a herb which supports balanced body systems by responding to the body's need for stimulation or relaxation.

Because the *Morinda citrifolia* fruit is for all practical purposes inedible, the fruit must be processed in order to make it palatable for human consumption and included in the naturaceutical used to treat fungal activity within the body. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other process include freeze drying the fruit and juice. The fruit and juice can be reconstituted during production of the final juice product. Still other processes include air drying the fruit and juices, prior to being masticated.

The present invention contemplates the use of fruit juice and/or puree fruit juice extracted from the *Morinda Citrifolia* plant and further processed into a naturaceutical formulation. Fruit juice or puree juice concentrate is also contemplated. In one exemplary embodiment, namely in regards to the process for producing *Morinda citrifolia* juice, the fruit is either hand picked or picked by mechanical equipment. The fruit can be harvested when it is at least one inch (2–3 cm) and up to 12 inches (24–36 cm) in diameter. The fruit may have a color ranging from a dark green through a yellow-green up to a white color, and gradations of color in between. The fruit is thoroughly cleaned after harvesting and before any processing of the juice occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit may be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp from the fruit may be packaged into containers for storage and transport. Alternatively, the juice and pulp can be immediately processed into a finished juice product. The containers may be stored in refrigerated, frozen, or room temperature conditions.

The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

In one embodiment, the product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181° F. (83° C.) minimum and then packed in drums for further processing or made into a high fiber product. Drying may further process the wet pulp. The methods of drying may include freeze-drying, drum drying, tray drying, sun drying, and spray drying. The dried *Morinda citrifolia* pulp may include a moisture content in the range from 0.1 to 15 percent by weight and more preferably from 5 to 10 percent by weight. The dried pulp preferably has a fiber content in the range from 0.1 to 30 percent by weight, and more preferably from 5 to 15 percent by weight.

The high fiber product may include wet or dry *Morinda citrifolia* pulp, supplemental fiber ingredients, water, sweeteners, flavoring agents, coloring agents, and/or nutritional ingredients. The supplemental fiber ingredients may include plant based fiber products, either commercially available or developed privately. Examples of some typical fiber products are guar gum, gum arabic, soybean fiber, oat fiber, pea fiber, fig fiber, citrus pulp sacs, hydroxymethylcellulose, cellulose, seaweed, food grade lumber or wood pulp, hemicellulose, etc. Other supplemental fiber ingredients may be derived from grains or grain products. The concentrations of these other fiber raw materials typically range from 0 up to 30 percent, by weight, and more preferably from 10 to 30 percent by weight.

Typical sweeteners may include, but are not limited to, natural sugars derived from corn, sugar beet, sugar cane, potato, tapioca, or other starch-containing sources that can be chemically or enzymatically converted to crystalline chunks, powders, and/or syrups. Also sweeteners can consist of artificial or high intensity sweeteners, some of which are aspartame, sucralose, stevia, saccharin, etc. The concentration of sweeteners may be between from 0 to 50 percent by weight, of the formula, and more preferably between about 1 and 5 percent by weight.

Typical flavors can include, but are not limited to, artificial and/or natural flavor or ingredients that contribute to palatability. The concentration of flavors may range, for example, from 0 up to 15 percent by weight, of the formula. Colors may include food grade artificial or natural coloring agents having a concentration ranging from 0 up to 10 percent by weight, of the formula.

Typical nutritional ingredients may include vitamins, minerals, trace elements, herbs, botanical extracts, bioactive chemicals and compounds at concentrations from 0 up to 10 percent by weight. Examples of vitamins one can add to the fiber composition include, but are not limited to, vitamins A, B1 through B12, C, D, E, Folic Acid, Pantothenic Acid, Biotin, etc. Examples of minerals and trace elements one can add to the fiber composition include, but are not limited to, calcium, chromium, copper, cobalt, boron, magnesium, iron, selenium, manganese, molybdenum, potassium, iodine, zinc, phosphorus, etc. Herbs and botanical extracts include, but are not limited to, alfalfa grass, bee pollen, chlorella powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The juice and pulp can be dried using a variety of methods. The juice and pulp mixture can be pasteurized or enzymatically treated prior to drying. The enzymatic process begins with heating the product to a temperature between 75° F. and 135° F. It is then treated with either a single enzyme or a combination of enzymes. These enzymes include, but are not limited to, amylase, lipase, protease, cellulase, bromelin, etc. The juice and pulp may also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice may be vacuum evaporated to a brix of 40 to 70 and a moisture of 0.1 to 80 percent, more preferably from 25 to 75 percent. The resulting concentrated *Morinda citrifolia* L. juice may or may not be pasteurized. For example, the juice would not be pasteurized in circumstances where the sugar content or water activity was sufficiently low enough to prevent microbial growth. It is packaged for storage, transport and/or further processing.

The Indian Mulberry plant or *Morinda citrifolia* is rich in natural ingredients. Those ingredients that have been discovered include: from the leaves—alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; from the flowers—acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; (from the fruit) acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthiopropanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; from the roots-anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; from the root bark—alizarin, chlororubin, glycosides (pentose, hexose), morindadiol, morindanigrine, morindine, morindone, resinous matter, rubiadin monomethyl ether, and soranjidiol; from the wood—anthragallol-2,3-dimethylether; and from the tissue culture—damnacanthal, lucidin, lucidin-3-primeveroside, and morindone-6beta-primeveroside; from the plant-alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothaches, blemishes, immune system failure, and others.

The compositions containing *Morinda citrifolia* may be in a form suitable for oral use, systemic administration, injection, and others. In regards to an oral composition, such a composition may exist, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

Favorably, this invention provides a method of treating and inhibiting fungal and other microbial activity or growth with a *Morinda citrifolia*-based naturaccutical formulation without any significant tendency to cause gastric side effects.

As used herein, the term *Morinda citrifolia* juice refers to a product that includes juice processed from the fruit of the Indian Mulberry or *Morinda citrifolia L.* plant. In one embodiment, *Morinda citrifolia* juice includes reconstituted fruit juice from pure juice puree of French Polynesia. The naturaceutical composition or formulation comprising at least one processed *Morinda citrifolia* product may also include other natural juices, such as a natural grape juice concentrate, a natural blueberry juice concentrate, and/or another natural juice concentrates. In a further embodiment, *Morinda citrifolia* juice is not processed from dried or powdered *Morinda citrifolia*.

*Morinda citrifolia*-based Naturaceutical Formulations and Methods of Administration for Inhibiting and Preventing Fungal Growth Within the Body The present invention advances fungal and other antimicrobial inhibitors by providing a naturaceutical composition formulated with one or more processed *Morinda citrifolia* products derived from the Indian Mulberry plant. The *Morinda citrifolia* is incorporated into various carriers or naturaceutical compositions suitable for in vivo treatment of a patient. For instance, the inhibitor may be ingested, injected, introduced intravenously, or otherwise internalized as is appropriate and directed.

In one exemplary embodiment, the naturaceutical composition of the present invention comprises one or more of a processed *Morinda citrifolia* (e.g. *Morinda citrifolia* fruit juice or fruit juice or puree juice) product present in an amount by weight between about 0.01 and 100 percent by weight, and preferably between 0.01 and 95 percent by weight. Several embodiment of formulations are provided below. However, these are only intended to be exemplary as one ordinarily skilled in the art will recognize other formulations or compositions comprising the processed *Morinda citrifolia* product.

The processed *Morinda citrifolia* product comprises at least one of the active ingredients in the naturaceutical, or contains one or more active ingredients, such as Quercetin and Rutin, and others, for effectuating the inhibition of fungal activity.

Active ingredients within the processed *Morinda citrifolia* product may be extracted out using various alcohol or alcohol-based solutions, such as methanol, ethanol, and ethyl acetate, and other alcohol-based derivatives using procedures and processes commonly known in the art. The active ingredients of Quercetin and Rutin are present in amounts by weight ranging from 0.01–10 percent of the total formulation or composition. If desired, these amounts may be concentrated into a more potent concentration in which they are present in amounts ranging from 10 to 100 percent.

The processed *Morinda citrifolia* product may be formulated with various other ingredients to produce various compositions, such as a naturaceutical composition, a topical dermal composition, or others. The ingredients to be utilized in a naturaceutical composition are any that are safe for introduction into the body of a mammal, and particularly a human, and may exist in various forms, such as liquids, tablets, lozenges, aqueous or oily solutions, dispersible powders or granules, emulsions, syrups, elixirs, etc. Moreover, since the naturaceutical composition is preferably consumed orally, it may contain one or more agents selected from the group consisting of sweetening agents, flavoring agents, coloring agents, preserving agents, and other medicinal agents as directed.

The ingredients to be utilized in a topical dermal composition are also any that are safe for internalizing into the body of a mammal and may exist in various forms, such as gels, lotions, creams, ointments, etc., each comprising one or more carrier agents. The ingredients for systemically (e.g. intravenously) administered formulations may also comprise any known in the art.

The present invention further features a method of administering a naturaceutical composition to a mammal to inhibit fungal activity within the body. In one exemplary embodiment, the method comprises the steps of (a) formulating a naturaccutical composition comprising in part a processed *Morinda citrifolia* product present in an amount between about 0.01 and 95 percent by weight, wherein the composition also comprises a carrier, such as water or purified water, and may also comprise other natural or artificial ingredients; (b) administering the naturaceutical composition into the body of a mammal, such that the processed *Morinda citrifolia* product is sufficiently internalized; (c) repeating the above steps as often as necessary to provide an effective amount of the processed *Morinda citrifolia* product needed to inhibit and/or prevent fungal and other microbial activity or growth.

The step of administering the naturaceutical composition into the body preferably comprises ingesting the composition orally through one of several means. Specifically, the naturaceutical composition may be formulated as a liquid, gel, solid, or some other type that would allow the composition to be quickly digested and concentrated within the colon. It is important to note that the step of administering the naturaceutical composition should be carried out in an effective manner so that the greatest concentration of naturaceutical composition is allowed to absorb into the tissues and cells. For the naturaceutical composition to take effect, it must be sufficiently internalized. Once sufficiently internalized, it may then begin to effectuate the inhibition and prevention of fungal and other microbial activity or growth.

In another embodiment, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition.

In one exemplary embodiment, the naturaceutical composition is administered by taking between 1 teaspoon and 2 oz., and preferably 2 oz., of the naturaceutical composition every two hours each day, or at least twice a day on a continued basis. Also, the naturaceutical composition is to be taken on an empty stomach, meaning at a period of time at least two hours prior to consumption of any food or drink. Of course, one ordinarily skilled in the art will recognize that the amount of composition and frequency of use may vary from individual to individual.

The following tables illustrate or represent some of the preferred formulations or compositions contemplated by the present invention. As stated, these are only intended as exemplary embodiments and are not to be construed as limiting in any way.

| Ingredients | Percent by Weight |
| --- | --- |
| Formulation One | |
| *Morinda citrifolia* puree juice or fruit juice | 100% |
| Formulation Two | |
| *Morinda citrifolia* fruit juice | 85–99.99% |
| Water | 0.1–15% |
| Formulation Three | |
| *Morinda citrifolia* fruit juice | 85–99.99% |
| non-*Morinda citrifolia*-based fruit juices | 0.1–15% |
| Formulation Four | |
| *Morinda citrifolia* fruit juice | 50–90% |
| water | 0.1–50% |
| non-*Morinda citrifolia*-based fruit juices | 0.1–30% |
| Formulation Five | |
| *Morinda citrifolia* puree juice | 85–99.9% |
| water | 0.1–15% |
| Formulation Six | |
| *Morinda citrifolia* puree juice | 85–99.9% |
| non-*Morinda citrifolia*-based fruit juices | 0.1–15% |
| Formulation Seven | |
| *Morinda citrifolia* puree juice | 50–90% |
| water | 0.1–50% |
| non-*Morinda citrifolia*-based fruit juices | 0.1–30% |
| Formulation Eight | |
| *Morinda citrifolia* dietary fiber | 0.1–30% |
| water | 1–99.9% |
| non-*Morinda citrifolia*-based fruit juices | 1–99.9% |
| Formulation Nine | |
| *Morinda citrifolia* dietary fiber | 0.1–30% |
| water | 1–99.9% |
| *Morinda citrifolia* fruit juice or puree juice | 1–99.9% |
| Formulation Ten | |
| *Morinda citrifolia* oil | 0.1–30% |
| carrier medium | 70–99.9% |
| other ingredients | 1–95% |
| Formulation Eleven | |
| *Morinda citrifolia* product | 10–80% |
| carrier medium | 20–90% |
| Formulation Twelve | |
| *Morinda citrifolia* product | 5–80% |
| carrier medium | 20–95% |

-continued

| Ingredients | Percent by Weight |
|---|---|
| Formulation Thirteen | |
| Morinda citrifolia oil or oil extract | 0.1–20% |
| carrier medium | 20–90% |
| Formulation Fourteen | |
| Morinda citrifolia puree juice or fruit Juice | 0.1–80% |
| Morinda citrifolia oil | 0.1–20% |
| carrier medium | 20–90% |
| Formulation Fifteen | |
| Morinda citrifolia puree juice concentrate or fruit juice concentrate | 100% |
| Formulation Sixteen | |
| Morinda citrifolia fruit juice concentrate or puree juice concentrate | 85–99.99% |
| Water | 0.1–15% |
| Formulation Seventeen | |
| Morinda citrifolia puree juice or fruit juice fraction | 100% |
| Formulation Eighteen | |
| Morinda citrifolia fruit juice fraction | 85–99.99% |
| Water | 0.1–15% |
| Formulation Nineteen | |
| Morinda citrifolia fruit juice fraction | 85–99.99% |
| non-Morinda citrifolia-based fruit juices | 0.1–15% |
| Formulation Twenty | |
| Morinda citrifolia fruit juice fraction | 50–90% |
| water | 0.1–50% |
| non-Morinda citrifolia-based fruit juices | 0.1–30% |
| Formulation Twenty One | |
| Morinda citrifolia puree juice fraction | 85–99.9% |
| water | 0.1–15% |
| Formulation Twenty Two | |
| Morinda citrifolia puree juice fraction | 85–99.9% |
| non-Morinda citrifolia-based fruit juices | 0.1–15% |

As stated, in one exemplary embodiment, the present invention features a method for introducing an internal composition or formulation to inhibit fungal and other microbial activity or growth. This method essentially comprises the introduction of a naturaceutical internal composition into the body of a mammal. Several embodiments of the internal composition comprising various different ingredients are contemplated for use, with each embodiment comprising one or more forms of a processed Morinda citrifolia product as taught and explained herein and a carrier agent or medium.

In one preferred method, microbial activity or growth is treated, prevented, destroyed, and/or reversed, by administering at least one (1) ounce of one of Formulations One through Sixteen above in the morning on an empty stomach, and at least one (1) ounce at night on an empty stomach, just prior to retiring to bed.

In one example, which is not meant to be limiting in any way, the beneficial Morinda Citrifolia is processed into TAHITIAN NONI® juice, a processed Morinda citrifolia product, manufactured by Morinda, Incorporated of Orem, Utah.

In an exemplary embodiment, the internal composition comprises the ingredients of: a processed Morinda citrifolia product present in an amount by weight between about 10–80 percent; and a carrier medium present in an amount by weight between about 20–90 percent.

In this embodiment, the processed Morinda citrifolia product may comprise one or more of a processed Morinda citrifolia fruit juice, processed Morinda citrifolia puree juice, processed Morinda citrifolia fruit or puree juice concentrate, processed Morinda citrifolia dietary fiber, and/or processed Morinda citrifolia oil extract product.

In another exemplary embodiment, the internal composition comprises the ingredients of: processed Morinda citrifolia fruit juice or puree juice present in an amount by weight between about 0.1–80 percent; processed Morinda citrifolia oil present in an amount by weight between about 0.1–20 percent; and a carrier medium present in an amount by weight between about 20–90 percent. Morinda citrifolia puree juice or fruit juice may also be formulated with a processed Morinda citrifolia dietary fiber product present in similar concentrations.

According to the present invention, the particular methods of introducing an internal composition may comprises any method of actually introducing the internal composition into the body of a mammal for the purposes identified herein. Although the particular methods are many, the present invention recognizes that the internal composition may be introduced intravenously, transdermally, orally, or systemically. No matter what method is employed, it is important to thoroughly internalize the composition so that the internal composition, and particularly the Morinda citrifolia and other active ingredients, can effectively inhibit or treat fungal and other microbial activity or growth.

The carrier medium identified in the above-identified Formulations may comprise any ingredient capable of being introduced into the body of a mammal, and that is also capable of providing the carrying medium to the processed Morinda citrifolia product. Specific carrier mediums formulations are well known in the art and not described in detail herein. The purpose of the carrier medium is as stated, to provide a means to embody the processed Morinda citrifolia product within the internal composition that is capable of being introduced into the body.

The following examples set forth and present the preventative and treatment effects of the processed Morinda citrifolia products on fungal activity. These examples are not intended to be limiting in any way, but are merely illustrative of the benefits and advantageous, as well as the remedial effects, of the Morinda citrifolia products.

EXAMPLE ONE

A study was conducted to determine the mean inhibitory concentrations of certain extracts from Morinda citrifolia against activity of common fungi and bacteria. In this study an attempt has been made to identify antimicrobial activity from Morinda citrifolia using a "top down" approach. Although somewhat infantile, a reproducible assay was developed, and initial studies have indicated that an antimicrobial component from Morinda citrifolia can be extracted.

In recent years, in an attempt to discover new antimicrobial compounds, many different sources have been explored. In short, in this study a Mean Inhibitory Concentration (MIC) protocol was developed and then used to test ethanol, methanol, and ethyl acetate extracts of Morinda citrifolia, for antifungal and antimicrobial activity against Aspergillus niger (ATCC 6275); Candida albicans (ATCC 10231); Trichophyton mentagrophytes (ATCC 9533); Staphlococcus aureus (ATCC 29213); and Escherichia coli (ATCC 25922).

Liquid extracts were obtained, and tested in microliter wells in duplicate. Quantities of the extracts, ranging from 6 ul to 200 μl, were placed in wells and dried. A McFarland 0.5 solution of each organism was prepared, and a 1/100 suspension into the appropriate media was made. This organism suspension was added to each well, and incubated for an appropriate amount of time at the appropriate temperature. Plates were then examined for growth, and MIC's were determined. All duplicate results agreed within one dilution. The ethyl acetate extracts had the least amount of antimicrobial activity, only showing activity when tested against *T. mentagrophytes* and *S. aureus*. The ethanol extracts showed antimicrobial activity against all of the organisms tested. This activity ranged from off-scale on the low end when tested against *T. mentagrophytes*, to high on-scale results for *A. niger*. Methanol extracts also had activity against all of the organisms tested, and ranged from off-scale on the low end when tested against *T mentagrophytes*, to high on-scale results for *A. niger*. These results indicate that at least some extracts of *Morinda citrifolia* contain antimicrobial activity. A more detailed description of this test follows.

The materials used in this test included several cultured microorganisms, namely, *S. aureus* ATCC 29213, *E. coli* ATCC 25922, *C. albicans* ATCC 10231, *T. mentagrophytes* ATCC 9533 and *A. niger* ATCC 6275. Initial cultures were developed as per the manufacturer's instructions. Prior to testing; *S. aureus* and *E. coli* were plated on Trypticase Soy Agar Plates, and incubated for 18–24 hours at 37° C. *C. albicans, T. mentagrophytes* and *A. niger* were plated on Saboraud Dextrose Agar plates, and incubated for 48–72 hours at 25° C.

For the microorganism suspension, microorganisms were used to prepare a 0.5 McFarland suspension in saline. 100 μl of the bacterial suspensions were added to 9.9 ml of Trypticase Soy Broth, and 100 μl of the fungal suspensions were added to 9.9 ml of Saboraud Dextrose Broth.

For the tray preparation, ethanol, methanol, and ethyl acetate extracts of *Morinda citrifolia*, were used in this study. *Morinda citrifolia* fruit juice extracts were supplied by Morinda, Inc. Each extract was used to prepare a row of microliter wells. Wells 1 and 6 received 200 μl of extract; wells 2 and 7 received 100 μl of extract; wells 3 and 8 received 50 μl of extract; wells 4 and 9 received 25 μl of extract; wells 5 and 10 received 12.5 μl of extract; and wells 6 and 12 received 6.3 μl of extract. This resulted in each row containing a duplicate series of extract material. Ethanol extracts were placed into rows A–B of a standard microliter tray, methanol extracts were placed into rows C–D of a standard microliter tray, and ethyl acetate extracts were placed into rows E–F of a standard microliter tray. Row G received 200 μl of 95% ethyl alcohol, and Row H received nothing. Trays were then incubated at 37° C. for 48 hours and allowed to dry.

Each microorganism was inoculated into a different tray using the 1/100 suspension of microorganism in media. 100 μls were added to each well. Following inoculation, bacterial isolates were incubated for 24–48 hours at 37° C. Fungal isolates were incubated for 72 hours at 25° C. Following incubation, wells were analyzed for growth. A minimal inhibitory concentration (MIC) was determined by noting the lowest concentration of extract that inhibited growth. Results were reported as microliters of extract in the well exhibiting the MIC. Rows G and H served as extract and growth controls.

Several problems had to be overcome in developing this assay. Perhaps the most difficult, was perfecting a method of drying the compounds in such a fashion as to allow them to be resolubilized after they were inoculated. A review of the history of the development of antimicrobials indicates that early experiments in which extracts of penicillin were dried resulted in the total loss of activity. This problem was solved by using low heat for an extended period of time.

The following Tables illustrate the discovered activity. Activity is reported as the smallest volume of dried extract capable of inhibiting growth.

TABLE 1

Activity of Ethanol Extracts

| | |
|---|---|
| *E. Coli* | 50 μl |
| *S. aureus* | 12.5 μl |
| *T. mentagrophytes* | ≦6.3–25 μl |
| *A. niger* | 100–200 μl |
| *C. albicans* | 100 μl |

TABLE 2

Activity of Methanol Extracts

| | |
|---|---|
| *E. Coli* | 25–50 μl |
| *S. aureus* | ≦6.3 μl |
| *T. mentagrophytes* | ≦6.3–12.5 μl |
| *A. niger* | 200 μl |
| *C. albicans* | 50–100 μl |

TABLE 3

Activity of Ethyl Acetate Extracts

| | |
|---|---|
| *E. Coli* | 200–>200 μl |
| *S. aureus* | 50–200 μl |
| *T. mentagrophytes* | 50–100 μl |
| *A. niger* | >200 μl |
| *C. albicans* | >200 μl |

TABLE 4

Extracts Tested with *E. Coli*

| | | | | |
|---|---|---|---|---|
| Ethanol | 50 | 50 | 50 | 50 |
| Methanol | 25 | 50 | 25 | 25 |
| Ethyl Acetate | >200 | >200 | 200 | >200 |

TABLE 5

Extracts Tested with *S. Aureus*

| | | | | |
|---|---|---|---|---|
| Ethanol | 12.5 | 12.5 | 12.5 | 12.5 |
| Methanol | ≦6.3 | ≦6.3 | ≦6.3 | ≦6.3 |
| Ethyl acetate | 50 | 50 | 200 | 200 |

TABLE 6

Extracts Tested with *T. Mentagrophytes*

| | | | | |
|---|---|---|---|---|
| Ethanol | ≦6.3 | 25 | ≦6.3 | 25 |
| Methanol | ≦6.3 | 12.5 | ≦6.3 | 12.5 |
| Ethyl acetate | 50 | 50 | 100 | 100 |

TABLE 7

| Extracts Tested with *A. Niger* | | | | |
|---|---|---|---|---|
| Ethanol | 200 | 200 | 100 | 100 |
| Methanol | 200 | 200 | 200 | 200 |
| Ethyl Acetate | >200 | >200 | >200 | >200 |

TABLE 8

| Extracts Tested with *C. Albicans* | | | | |
|---|---|---|---|---|
| Ethanol | 100 | 100 | 100 | 100 |
| Methanol | 100 | 100 | 50 | 50 |
| Ethyl Acetate | >200 | >200 | >200 | >200 |

The results of the test showed that activity of Ethanol extracts ranged from $6.3$ μl to 200 μl; the activity of Methanol extracts ranged from $6.3$ μl to 200 μl; the activity of Ethyl Acetate extracts ranged from 50 ul to 200 μl; and that ethanol and methanol extracts were the most effective against all of the microorganisms tested.

This study attempts to take the first steps at isolating new antimicrobial compounds from a raw material. This "top down" approach utilized crude extracts of *Morinda citrifolia*. Results indicated that the ethanol and methanol had activity against all of the microorganisms tested, which further indicated the antifungal activity of *Morinda citrifolia*.

With the demonstration of antimicrobial activity, it can be said that there exists at least one and possibly several compounds within *Morinda citrifolia* that are responsible for the antimicrobial activity exhibited herein. As such, other tests and experiments will become necessary to specifically identify and isolate these. Most likely, future research will involve purifying the extracts discussed herein using standard separation techniques, which will involve defining some of the myriad of compounds that are present in these extracts. Once isolated, each can be tested for antimicrobial activity.

In conclusion, ethanol, methanol and ethyl acetate extracts of *Morinda citrifolia* were found to exhibit antimicrobial activity when tested against *S. aureus, E. coli, C. albicans, T. mentagrophytes* and *A. niger.*

EXAMPLE TWO

The purpose of this experiment was to determine the mean inhibitory concentration (MIC) of selected *Morinda citrifolia* fruit juice extracts against three common pathogenic fungi and two common bacteria.

The organism used were *Aspergillus niger* (ATCC 6275); *Candida albicans* (ATCC 10231); *Trichophyton mentagrophytes* (ATCC 9533); *Staphlococcus aureus* (ATCC 29213); and *Escherichia coli*(ATCC 9533).

For the *Morinda citrifolia* fruit juice extracts, ethanol, methanol, ethyl acetate, and aqueous extracts of were prepared using the appropriate solvents.

The sterile media preparations (1 liter) included: for fungi, a Sabouraud Dextrose Broth (SDB); for bacteria, a Mueller Hinton Broth (MHB); autoclave at 121° C. for 20 minutes.

The organism suspension preparations included plating each organism on appropriate media, incubate and confirm identity, prepare a 0.5 McFarland suspension of each organism, and add 0.1 ml of the organism to 9.9 ml of the appropriate media (SDB or MHB).

To prepare the *Morinda citrifolia* juice extracts, using the appropriate media, the extracts were dried and then diluted to a final concentration of 2 mg/ml. The extracts were then stored in −20° C. freezers until ready for fungal plating. These 2 mg/ml final volumes were used as *Morinda citrifolia* stock solutions.

Thirteen test tubes were labeled as follows:

| | | |
|---|---|---|
| 1/1 | 1/32 | 1/512 |
| 1/2 | 1/64 | 1/1024 |
| 1/4 | 1/128 | Growth control |
| 1/8 | 1/256 | Non-inoculated control |
| 1/16 | | |

100 μl of *Morinda citrifolia* stock solution was added to Tube 1/1 and 100 μl to Tube 1/2. 100 μl of sterile media was added to Tubes: 1/2, 1/4, 1/8, 1/16, 1/32, 1/64, 1/128, 1/256, 1/512, 1/1024, Growth control, and Non-inoculated control.

Tube 1/2 was mixed well and 100 μl removed and added to Tube 1/4. This two-fold dilution procedure was continued for Tubes 1/8, 1/16, 1/32, 1/64, 1/128, 1/256, 1/512, and 1/1024. Discard 100 μl from Tube 1/1024. No diluted *Morinda citrifolia* solutions were added to Tubes GC or NC. These were the control tubes. At this point all tubes contained 100 μl.

Because we know that we started with 2 mg/ml (i.e. 2000 μg/ml) of extract stock solution, the serial two fold dilution resulted in the following concentrations of *Morinda citrifolia* fruit juice extract as shown in the table below.

| Tube # | Dilution | Concentration of Extract |
|---|---|---|
| 1 | 1/1 | 2000 μg/ml |
| 2 | 1/2 | 1000 μg/ml |
| 3 | 1/4 | 500 μg/ml |
| 4 | 1/8 | 250 μg/ml |
| 5 | 1/16 | 125 μg/ml |
| 6 | 1/32 | 62.50 μg/ml |
| 7 | 1/64 | 31.25 μg/ml |
| 8 | 1/128 | 15.13 μg/ml |
| 9 | 1/256 | 7.56 μg/ml |
| 10 | 1/512 | 3.78 μg/ml |
| 11 | 1/1024 | 1.89 μg/ml |
| 12 | GC | No extract |
| 13 | NC | No organism |

During inoculation, 100 μl of organism suspension were added to all of the tubes expect Tube Non-inoculated control (NC). 100 μl of additional media was added to NC. All tubes were incubated at the appropriate temperatures and intervals—for fungi, 25° C. for 5–7 days; for bacteria, 37° C. for 24–48 hours.

The results were recorded by observing turbidity. The presence of turbidity indicated growth, while the absence of turbidity indicated inhibition of growth. For any extract, a result was valid only if there was turbidity (i.e. growth) in the Tube Growth control, and no turbidity in the Tube Non-inoculated control (i.e. no growth). The MIC was determined as the last tube in the series (i.e. the most diluted tube) with no turbidity.

The following represents the mean inhibitory concentration (μg/ml):

|  | EtOH | MeOH | EtAc |
|---|---|---|---|
| C. albicans | 1000 | 250–1000 | >2000 |
| A. niger | 1000–2000 | 1000–2000 | >2000 |
| T. mentagr. | ≴7.56 | ≴7.56 | 250–1000 |
| S. aureus | 31.25–62.50 | 31.25–62.50 | 1000–2000 |
| E. coli | 250 | 62.50–250 | >2000 |

Results indicate that the ethanol and methanol *Morinda citrifolia* extracts had meaningful activity against all of the microorganisms tested. Preliminary drying studies indicated that the activity using the ethanol and methanol extracts was in the 5–10 mg/ml range. Ethyl acetate extracts contained <10% of the amount found in the ethanol and methanol extracts.

From this initial phase of the study, it can clearly be established that *Morinda citrifolia* fruit juice or the extracts thereof exhibit a substantial amount of antifungal activity. However, each extract contains hundreds of compounds. Indeed, at 1000 μl/ml, there may be 100 compounds at concentrations of 10 μl/ml each. Thus, since the extracts tested were not purified antimicrobial compounds, even very high MIC's may be meaningful. Later tests described below set forth some specific compounds that were fractioned or extracted out of *Morinda citrifolia* fruit juice concentrate.

EXAMPLE THREE

For the following experiment, the minimum inhibitory concentration (MIC) of an antibacterial is defined as the maximum dilution of the product that will still inhibit the growth of a test microorganism. The minimum lethal concentration (MLC) of an antibacterial is defined as the maximum dilution of the product that killed a test organism. MIC/MLC values can be determined by a number of standard test procedures. The most commonly employed methods are the tube dilution method and agar dilution methods. The tube dilution method was proposed for this product to determine the MIC, and plating aliquots from dilutions demonstrating possible inhibition of growth to determine the MLC. Serial dilutions were made of the products in bacterial growth media. The test organisms were added to the dilutions of the products, incubated, and scored for growth. All tests were performed in triplicate.

This procedure is a standard assay for antimicrobials. The procedure incorporates the content and intent of the American Society for Microbiology (ASM) recommended methodology. The tube dilution method employs dilutions of the test product in a bacterial growth media, inoculation with a predetermined test organism concentration, and visualization of growth after incubation. Tube dilution procedures are limited to products which do not precipitate or cloud the growth media within the expected endpoint range.

For the culture preparation procedure, the test organisms used were *Escherichia coli* 0157H7 ATCC #43888; *Staphylococcus aureus* ATCC #6538; *Bacillus subtilis* ATCC #19659; *Salmonella choleraesuis* serotype *enteritidis* ATCC #13706; *Listeria monocytogenes* ATCC #19111; *Candida albicans* ATCC #10231; and *Streptococcus mutans* ATCC #25175.

From stock, the test organisms were transferred to soybean casein digest broth (SCDB) and incubated at 37±2° C. for 24–48 hours for bacteria, and 20–25° C. for yeast. If needed, the suspensions were adjusted to approximately $10^8$ colony forming units (CFU) per mL, by visual turbidity, in physiological saline solution (PHSS) and a standard plate count was performed to determine starting titers. The yeast culture was plated onto Sabouraud dextrose agar (SDEX) and incubated at 20–25° C. for 2–4 days, *S. mutans* was incubated at 37±2° C. for 3–5 days, and all other bacteria were incubated at 37±2° C. for 18–24 hours.

For the Mean Inhibitory Concentration (MIC) test procedure, the test product was adjusted to a neutral pH for the purpose of this test. The pH was recorded before and after adjustments had been made. Each test product was diluted 1:2 serially in sterile water. Dilutions were selected that would show the MIC/MLC endpoint. Each test product evaluation was performed in triplicate for each organism. The product dilutions were added to an equal volume of 2×SCDS to provide an additional 1:2 dilution. Three positive control tubes were prepared for each test organism by mixing sterile water with equal volumes of 2×SCDB. Three negative control tubes were prepared by mixing the highest dilution tested of the test product with equal volumes of 2×SCDB. No test organisms were added to these tubes. Three media control tubes were prepared by mixing sterile water with equal volumes of 2×SCDB. No test organisms were added to these tubes either.

Approximately 0.05 mL of each test organism suspension was added to the sample and positive control tubes. The bacteria test tubes were incubated at 37±2° C. for 18–24 hours and yeast test tubes were incubated at 20–25° C. for 2–4 days. After incubation, growth was scored as negative (0) or positive (+) for each tube.

For the Mean Lethal Concentration (MLC) test procedure, only tubes suspected of not having any growth were tested. A 1.0 mL aliquot was removed from each tube and serial 1/10 dilutions were made in neutralizer broth up to 1/1000. An aliquot of each dilution was plated on neutralizer agar (NUAG). For a positive control, 10–100 CFU were plated onto NUAG. A negative control was made by plating 2×SCDB onto NUAG. The plates were incubated 20–25° C. for 2–4 days for yeast, and 37±2° C. for 18–24 hours for all bacteria except for *S. mutans*.

With regards to what is known as neutralization verification, the lowest dilution of the test product tested for MLC was tested for neutralization recovery for each test organism. In triplicate, 0.5 mL aliquots of the most concentrated test product were plated on NUAG. The plates were spiked with 10–100 CFU of each test organism. For comparison, three plates of NUAG without the test product were also spiked with the same 10–100 CFU for each of the test organisms.

The results were as follows. With the exception of *S. mutans*, all organisms were inhibited by neutralized *Morinda citrifolia* concentrate at a 1:2 concentration. None of the dilutions tested were able to demonstrate lethality for any of the organisms. Neither inhibition nor lethality was demonstrated by the neutralized *Morinda citrifolia* concentrate when tested against *S. mutans*.

The MIC results for all organisms are summarized in Tables 1–7. The MLC results for each organism are summarized in Tables 8–13. Since *S. mutans* did not have any dilutions that were scored as having no growth for the MIC portion of the test, MLC was not performed for this organism.

The neutralization recoveries for all test organisms ranged from 40–97%. The neutralization recovery of the neutralizing media used in the study is summarized in Table 14.

TABLE 1

Mean Inhibitory Concentration Results for
*Escherichia coli* O157H7 ATCC #43885

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $7.0 \times 10^8$ CFU/mL

Inoculating volume=0.05 mL

TABLE 2

Mean Inhibitory Concentration Results for
*Staphylococcus aureus* ATCC #6538

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $6.5 \times 10^8$ CFU/mL

Inoculating volume=0.05 mL

TABLE 3

Mean Inhibitory Concentration Results for
*Bacillus subtilis* ATCC #19659

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $8.5 \times 10^7$ CFU/mL

Inoculating volume=0.05 mL

TABLE 4

Mean Inhibitory Concentration Results for
*Salmonella choleraesuis* serotype *enteritidis* ATCC #13706

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| Positive | + | + | + |
| Negative | 0 | 0 | 0 |
| Media | 0 | 0 | 0 |

Titer: $4.8 \times 10^8$ CFU/mL

Inoculating volume=0.05 mL

TABLE 5

Mean Inhibitory Concentration Results for
*Listeria monocytogenes* ATCC #19111

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $3.9 \times 10^8$ CFU/mL

Inoculating volume=0.05 mL

TABLE 6

Mean Inhibitory Concentration Results for
*Candida albicans* ATCC #10231

| DILUTION | GROWTH +/0 | | |
|---|---|---|---|
| 1:2 | 0 | 0 | 0 |
| 1:4 | + | + | + |
| 1:8 | + | + | + |
| 1:16 | + | + | + |
| 1:32 | + | + | + |
| 1:64 | + | + | + |
| Positive | + | + | + |
| Negative | 0 | 0 | 0 |
| Media | 0 | 0 | 0 |

Titer: $1.3 \times 10^8$ CFU/mL

Inoculating volume=0.05 mL

TABLE 7

Mean Inhibitory Concentration Results for
*Streptococcus mutans* ATCC #25175

| DILUTION | GROWTH +/0 | | |
|---|---|---|---|
| 1:2 | 0 | 0 | 0 |
| 1:4 | + | + | + |
| 1:8 | + | + | + |
| Positive | + | + | + |
| Negative | 0 | 0 | 0 |
| Media | 0 | 0 | 0 |

Titer: $1.0 \times 10^7$ CFU/mL

Inoculating volume=0.05 mL

TABLE 8

Mean Lethal Concentration Results for *Escherichia coli* 015H7 ATCC #43588

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | TNTC | TNTC | TNTC | 245 |
| | 2 | TNTC | TNTC | TNTC | 239 |
| | 3 | TNTC | TNTC | TNTC | 215 |

Volume plated=0.5 mL

TNTC=Too Numerous To Count

TABLE 9

Mean Lethal Concentration Results for *Staphylococcus aureus* ATCC #6538

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | TNTC | TNTC | TNTC | 200 |
| | 2 | TNTC | TNTC | TNTC | 134 |
| | 3 | TNTC | TNTC | TNTC | 114 |

Volume plated=0.5 mL

TNTC=Too Numerous To Count

TABLE 10

Mean Lethal Concentration Results for *Bacillus subtilis* ATCC #19659

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | 27 | 3 | 0 | 0 |
| | 2 | 25 | 2 | 0 | 0 |
| | 3 | 18 | 2 | 0 | 0 |

Volume plated=0.5 mL

TABLE 11

Mean Lethal Concentration Results for *Salmonella choleraesuis* serotype *enteritidis* ATCC #13706

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | TNTC | TNTC | 41 | 7 |
| | 2 | TNTC | TNTC | 75 | 5 |
| | 3 | TNTC | TNTC | 63 | 6 |

Volume plated=0.5 mL

TNTC=Too Numerous To Count

TABLE 12

Mean Lethal Concentration Results for *Listeria monocytogenes* ATCC #19111

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | TNTC | TNTC | TNTC | 109 |
| | 2 | TNTC | TNTC | TNTC | 109 |
| | 3 | TNTC | TNTC | TNTC | 179 |

Volume plated=0.5 mL

TNTC=Too Numerous To Count

TABLE 13

Mean Lethal Concentration Results for *Candida albicans* ATCC #10231

| | | DILUTION | | | |
|---|---|---|---|---|---|
| DILUTION | REPLICATE | $10^0$ | $10^{-1}$ | $10^{-2}$ | $10^{-3}$ |
| 1:2 | 1 | TNTC | TNTC | TNTC | 168 |
| | 2 | TNTC | TNTC | TNTC | 117 |
| | 3 | TNTC | TNTC | TNTC | 138 |

Note: Volume plated=0.5 mL

TNTC=Too Numerous To Count

TABLE 14

| | Neutralization | | | | | | | | |
|---|---|---|---|---|---|---|---|---|---|
| | POSITIVE COUNT | | | | NEUTRALIZATION COUNT | | | | PERCENT |
| ORGANISM | 1 | 2 | 3 | AVE | 1 | 2 | 3 | AVE | RECOVERY |
| *E. coli* 0157H7 | 60 | 63 | 58 | 60 | 53 | 50 | 73 | 59 | 97% |
| *S aureus* | 48 | 65 | 38 | 50 | 49 | 44 | 42 | 45 | 89% |

TABLE 14-continued

| | Neutralization | | | | | | | | |
|---|---|---|---|---|---|---|---|---|---|
| | POSITIVE COUNT | | | | NEUTRALIZATION COUNT | | | | PERCENT |
| ORGANISM | 1 | 2 | 3 | AVE | 1 | 2 | 3 | AVE | RECOVERY |
| B. subtilis | 53 | 61 | 53 | 56 | 25 | 20 | 22 | 22 | 40% |
| S. choleraesuis | 38 | 43 | 36 | 39 | 34 | 34 | 31 | 33 | 85% |
| L. monocytogenes | 43 | 38 | 22 | 34 | 26 | 31 | 34 | 30 | 88% |
| C. albicans | 36 | 25 | 21 | 27 | 20 | 12 | 27 | 20 | 72% |
| S. mutans | 11 | 19 | 13 | 14 | 9 | 16 | 14 | 13 | 91% |

EXAMPLE FOUR

In the previous examples, it was shown that a *Morinda citrifolia* product had inhibitory and preventative effects on fungus and microbials, or rather that the *Morinda citrifolia* products exhibited antifungal and antibacterial or antimicrobial activity. The following exemplary experiment takes the previous experiments even further to actually identify the one or more specific compounds or fractions existing within the several *Morinda citrifolia* product(s) that is/are responsible for effectuating antifungal activity within the body once introduced therein.

This example illustrates how the *Morinda citrifolia* products were fractioned. The experimental product was *Morinda citrifolia* fruit juice. Specifically, the *Morinda citrifolia* fruit juice was fractioned to obtain *Morinda citrifolia* n-hexane fractions, *Morinda citrifolia* $CL_2CL_2$, *Morinda citrifolia* ETOAc fractions, and *Morinda citrifolia* BuOH fractions, each of a specific concentration. Each of these were studied to determine their antimicrobial activity using the *Aspergillus niger* (ATCC 6275); *Candida albicans* (ATCC 10231); *Staphlococcus aureus* (ATCC 29213); and *Escherichia coli*(ATCC 9533) organisms. Other *Morinda citrifolia* products may also be fractioned in a similar manner as described herein.

In preparation, each extract was tested by preparing a series of concentrations in a microtiter tray. The first well of each series received 200 μl, the second 100 μl, the third 50 μl, the fourth 25 ul, the fifth 12.5 μl, and the sixth 6.3 μl. Trays were incubated at 35–37° C. for 72 hours. At this time all of the extracts had dried.

For the preparation of the organisms, ATCC isolate was plated on an appropriate media, and incubated. Following incubation, a 0.5 McFarland suspension of the organism was prepared in saline. 100 μl of this suspension was added to 9.9 ml of the appropriate media.

200 μl of the organism suspension were added to each well of the series, and used to suspend test material. An empty well was inoculated to serve as a growth control, and one well was inoculated with media to serve as a negative control.

Trays were incubated at the appropriate temperatures, for the appropriate intervals. (For the bacterial samples this was 35+/−2° C. for 24–48 hours. For fungi this was 20–25° C. for 5–7 days).

The growth control well was observed for the presence of turbidity, and the negative control was observed for the absence of turbidity (a result was only valid, if there was growth in the Growth Control well, and no growth in the non-inoculated well). Following this, each of the other wells were observed for the presence of turbidity. Results were recorded. The trays were then placed on a Multiskan Plate reader. Absorbance at 550 nm was recorded.

The minimum inhibitory concentration (MIC) was the last tube in the series, which was not turbid. The results of the test are presented below in the following tables, where activity is reported as mg/ml.

TABLE 1

Activity of *Morinda citrifolia* fruit juice concentrate

| E. Coli | 25 mg |
|---|---|
| S. aureus | 25 mg |
| A. niger | >50 mg |
| C. albicans | 50 mg |

TABLE 2

Activity of *Morinda citrifolia* hexane fraction

| E. Coli | 25 mg |
|---|---|
| S. aureus | 25 mg |
| A. niger | 25 mg |
| C. albicans | 12.5 mg |

TABLE 3

Activity of *Morinda citrifolia* ETOAc fraction

| E. Coli | 6.3 mg |
|---|---|
| S. aureus | 3.1 mg |
| A. niger | 25 mg |
| C. albicans | 12.5 mg |

TABLE 4

Activity of *Morinda citrifolia* n-BuOH fraction

| E. Coli | >12.5 mg |
|---|---|
| S. aureus | 25 mg |
| A. niger | >50 mg |
| C. albicans | >50 mg |

From these results, it shows that several of the *Morinda citrifolia* fractions and extracts exhibited inhibitory and preventative activity against the organisms being tested.

Two problems were encountered in this study. The first is that there was a problem getting some of the higher concentrations of the ETOAc fractions or extracts into solution. As a result when these were read, precipitation was observed. This precipitation did not interfere with the visual readings, but did interfere with the absorbance measure ments. A second problem is that the n-hexane fractions or extracts appeared to etch the plastic in the microtiter plate. This too caused problems with the absorbance, but not the visual readings.

Due to a lack of supplied compounds, the fourth tray did not have sufficient n BuOH to prepare all of the concentrations. As a result the *E. coli* result is reported as >12.5 mg/ml.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A formulation for inhibiting fungal and microbial growth within a mammal, said formulation comprising:

Quercetin between about 0.01 and 50 percent by weight;

*Morinda citrifolia* oil between about 0.1 and 30 percent by weight; and processed *Morinda citrifolia* puree juice between about 0.01 and 99.9 percent by weight.

2. The formulation of claim 1, wherein said processed formulation further comprises Rutin as an additional active ingredient.

3. The formulation of claim 2, wherein said Rutin is present in an amount between about 0.1 and 10 percent by weight.

4. The formulation of claim 1, wherein said formulation is administered via a method selected from the group consisting of orally, transdermally, by injection into said infected area, intravenously, and systemically.

* * * * *